United States Patent [19]

Hubbard et al.

[11] Patent Number: 4,565,301

[45] Date of Patent: Jan. 21, 1986

[54] DEVICE FOR DISPENSING RADIOACTIVE GAS

[75] Inventors: Robert E. Hubbard, Pleasant Hill; Robert C. Wedemeyer, Menlo Park, both of Calif.

[73] Assignee: Medi-Physics, Inc., Emeryville, Calif.

[21] Appl. No.: 387,104

[22] Filed: Jun. 10, 1982

[51] Int. Cl.⁴ .............................................. A61B 6/00
[52] U.S. Cl. ..................... 222/5; 222/83.5; 222/209; 222/325; 222/400.8; 128/203.21; 604/235
[58] Field of Search .............. 222/5, 83.5, 86, 88, 222/209, 325, 400.8; 128/1.2, 203.21; 604/235; 431/142, 344; 137/318

[56] References Cited

U.S. PATENT DOCUMENTS

| | | | |
|---|---|---|---|
| 2,593,552 | 4/1952 | Folkman | 222/5 |
| 2,596,447 | 5/1952 | Sundholm | 222/88 X |
| 3,848,773 | 11/1974 | Adler et al. | 222/1 |
| 4,081,006 | 3/1978 | Crowell | 222/83.5 X |
| 4,192,438 | 3/1980 | Foster et al. | 222/5 |

FOREIGN PATENT DOCUMENTS 2809823  9/1978  Fed. Rep. of Germany ...... 137/318

Primary Examiner—Joseph J. Rolla
Assistant Examiner—Frederick R. Handren
Attorney, Agent, or Firm—Jon S. Saxe; George M. Gould; William H. Epstein

[57] ABSTRACT

A device suitable for dispensing a radioactive gas from a sealed radioactive gas-containing vial having a pierceable septum wherein the dispenser contains two needles which pierce the septum, one of the needles conducting the radioactive gas from the vial into the dispenser and the other for the introduction of a displacement gas to the vial. The improvement being a means in the dispenser whereby the septum is automatically released from the needles without handling the vial so that the vial may be removed from the dispenser.

12 Claims, 4 Drawing Figures

DEVICE FOR DISPENSING RADIOACTIVE GAS

BACKGROUND AND DISCUSSION OF THE PRIOR ART

In the field of nuclear medicine, it is common to utilize radioactive gases such as xenon for conducting ventilation studies upon a patient. Generally, the xenon is administered to the patient by devices adapted to dispense the radioactive gas from a sealed vial containing this gas. These vials are contained within a radioactive shield to prevent comtamination of the atmosphere with the radioactive gas. Among the devices for dispensing radioactive gas are the dispensing devices disclosed in U.S. Pat. No. 3,848,773—Adler and U.S. Pat. No. 4,192,438—Foster et al. These devices utilize needles for piercing the septum of the vial containing the radioactive gas. One of the needles is utilized to feed the radioactive gas out of the vial to the patient while the other needle is utilized to inject a displacement gas such as air into the vial to force its radioactive contents outward. In carrying out this operation, the radioactive gas in the dispenser is generally sealed from the atmosphere so that the operation of dispensing the gas from the vial takes place without leakage.

One of the disadvantages of these devices is that after the radioactive gas from the vial is dispensed, the vial must be removed from the dispenser by hand in order to dislodge the needle from the septum. This action, which is carried out by hand, may subject the user to repeated exposure to radioactive gas. As is generally known, the administration of radioactive material to a patient should be carried out with as little handling as possible in order to avoid exposing the technician to the effects of radiation.

SUMMARY OF INVENTION

In accordance with this invention, a device for dispensing radioactive gas from a sealed vial in a protective casing having a pierceable septum is provided which minimizes handling problems and exposure of the technicians utilizing this device to radioactivity. This device comprises a dispenser and two needle means having ends protruding from the dispenser, which ends are adapted to pierce a septum. The first needle means is connected to an outlet for said radioactive gas, while the second needle means is connected to an inlet for providing a displacement gas to force the radioactive gas out of the vial and into the dispenser. The dispenser includes a spring means located in the dispenser which activates a moveable elongated member protruding from the dispenser, which elongated member has an opening at one end. This opening surrounds the protruding ends of both of the needle means and is configured to fit into the protective casing containing the vial so as to engage the vial within this opening. The vial is engaged within the opening of the elongated member with means provided by said elongated member to position the septum of the vial on both of the needle means so that the needle means pierce the septum and extend into the vial. When the needle means are positioned to pierce the septum and extend into the vial, the spring means is depressed against motion by a releasable locking means which maintains the vial within the dispenser positioned against the action of the spring means so that both of said protruding ends of the needle means pierce the septum. Upon release of this locking means, the spring action is free to move the elongated member containing the vial to disengage the septum from the needles so that the protruding ends of the needle means no longer pierce the septum and the vial is automatically removed from engagement with the needle means. In this manner, the vial and lead shield can be easily removed from the dispenser with minimum handling.

DETAILED DESCRIPTION OF THE INVENTION

In the drawing, which reference will be made in the specification, similar reference characters have been employed to designate corresponding parts throughout the several views.

Figure 1:
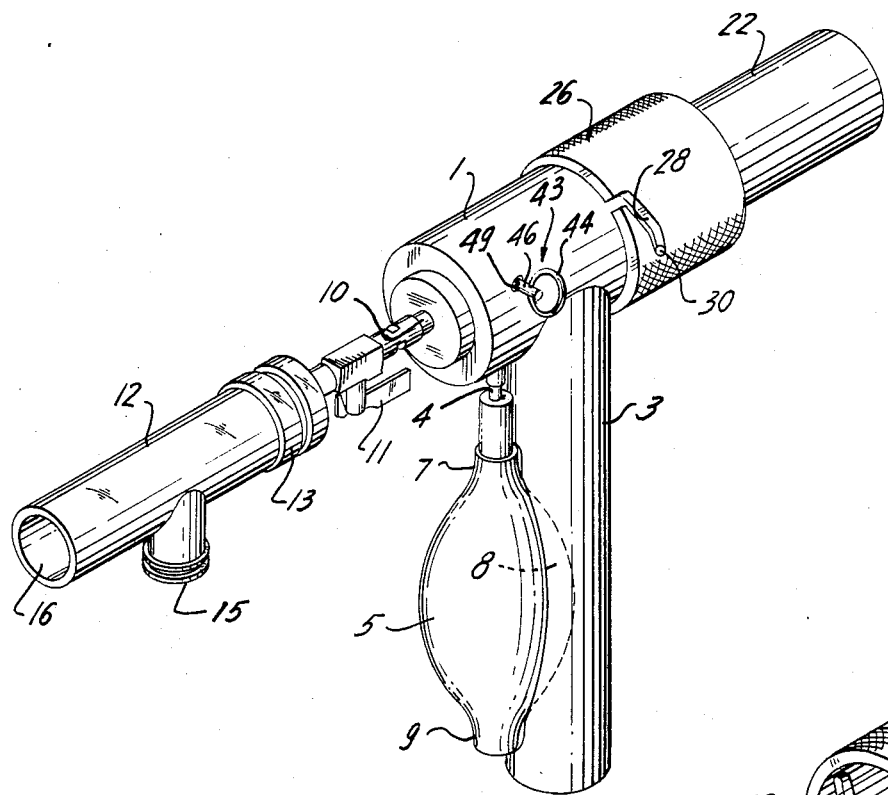
FIG. 1 is a perspective view of the dispenser engaging the vial and attached to a breathing adapter in accordance with one embodiment of the invention.

FIGS. 1 through 4 show one specific embodiment of the dispensing device of this invention which is used to dispense a premeasured dose of a radioactive gas. Generally this device is utilized for dispensing radioactive gases such as xenon which is used for ventilation or other diagnostic studies. FIG. 1 shows an embodiment of the dispensing mechanism of this invention. As can be seen from this embodiment, the device of this invention includes a dispenser 1 having a handle 3 which is rigid and extends outwardly from the bottom of the dispenser 1. This handle 3 is shaped to provide a hand-gripping surface. The dispenser 1 contains an inlet in the form of an adapter 4 to provide a displacement gas into the dispenser 1. The adapter 4 is shown as a lure fitting for attachment to the top portion 7 of a flexible bulb 5. Generally it is preferred that this gaas be air. As a source for the air, the flexible bulb 5 is provided which is attached to the air intake adapter 4. In accordance with a preferred embodiment, the flexible bulb 5 is constructed so to contain a one-way valve (not shown) located at position 9 to permit air to enter the bulb 5 and prevent any reversible flow thereof at position 9. Additionally, a check valve exists at position 6 to prevent any reversible flow into the bulb 5 or any gas supply system.

Bulb 5 rests adjacent the handle 3 which contains a recess 8. This recess provides a means for holding the bulb and the handle 3 manually and allowing the bulb 5 to collapse against the handle 3 also manually. By squeezing the bulb 5 against the handle 3, the bulb may be collapsed against the surface of the handle 3. The bulb is also provided at its bottom portion 9 with a one-way valve (not shown) to permit the intake of air to the bulb after collapsing the bulb 5.

The dispenser 1 also contains a gas-outlet means 10 in the form of an adapter through which the xenon gas is emitted from the dispenser 1. The adapter 10 is a lure fitting to attach to a valve 11 which permits the radioactive gas to flow out of the dispenser 1 into a breathing adapter 12. The breathing adapter 12 has a one-way valve (not shown) at its top portion 13. This one-way valve permits xenon to flow out of the dispenser 1 through valve 11 and into the breathing adapter 12 while preventing any reverse flow back through valve 11 and into the dispenser 1. The breathing adapter has two outlets 15 and 16. Outlet 15 is for connection by means of tubing to a breathing apparatus for the patient. Outlet 16 can be connected by tubing to a collection bag (not shown) so as to collect any excess radioactive gas which is not breathed in by the patient.

Figure 2:
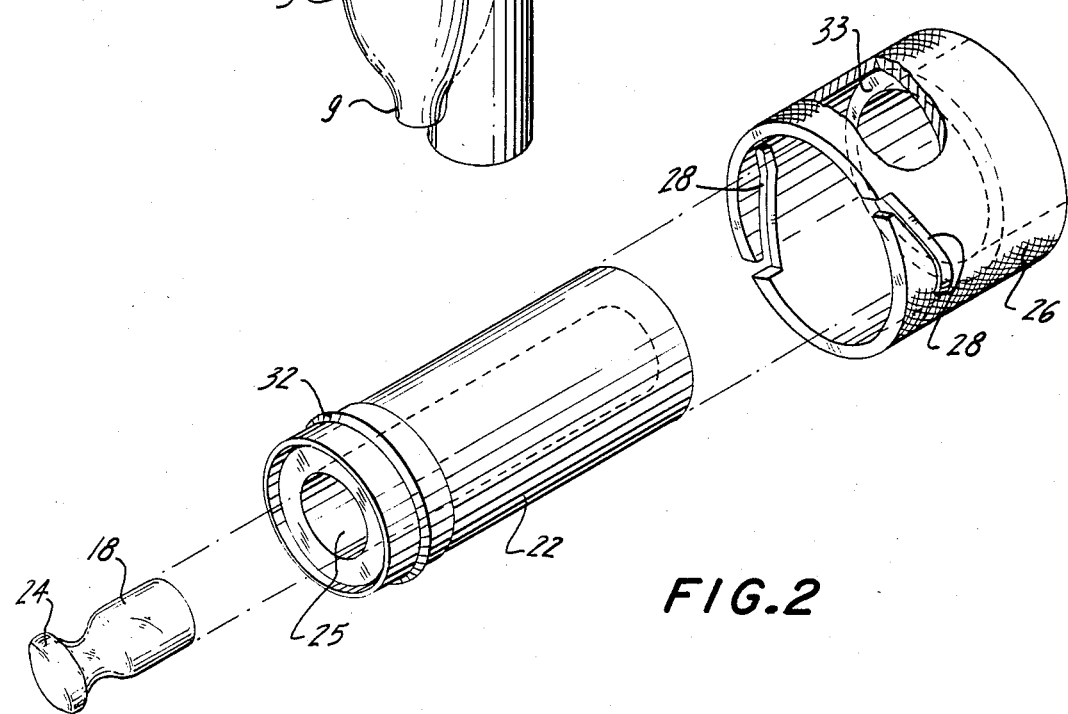
FIG. 2 is an exploded perspective view of the vial, its protective casing and ring member in accordance with one embodiment of this invention.

The vial 18 which contains premeasured amounts of radioactive gas is generally shipped and packaged in a protective casing or shield 22 which is generally lead. As seen in FIG. 2, the vial is sealed into the protective casing 22 by means of a lead cap (not shown). The outer surface of casing 22 contains a lip 32 for engaging the hollow ring 26. The lead cap may be removed just prior to use to expose the septum 24 of the vial 18 in the casing 22. The septum is made of a pierceable elastomeric material. The septum is formed from a material selected to have low absorption characteristic relative to the gas contained within the vial. Therefore, this material should absorb as little as possible of the gas and minimize the amount of gas which is so absorbed and which ultimate permeates through the septum, subsequently to become lost to the atmosphere. The material which forms the septum is further selected to provide as low a capillary leakage of gas as possible from the vial at the interface between the septum and the vial body. Materials which have been successfully used for this purpose are butyl elastomer materials and fluorinated hydrocarbon materials.

Upon removal of the lead cap (not shown), the protective casing is exposed so that the septum of the vial is adjacent to this opening 25 for insertion into the dispenser 1. In packaging the vial 18 in the casing or shield 22, the septum 24 is positioned at the open end 25 which is closed by the lead cap. Therefore, removal of the lead cap exposes the septum 24. Therefore, the vial 18 is positioned in the protective casing so that the septum 24 will be adjacent the opening 25 when the protective lead cap is removed.

Figure 4:
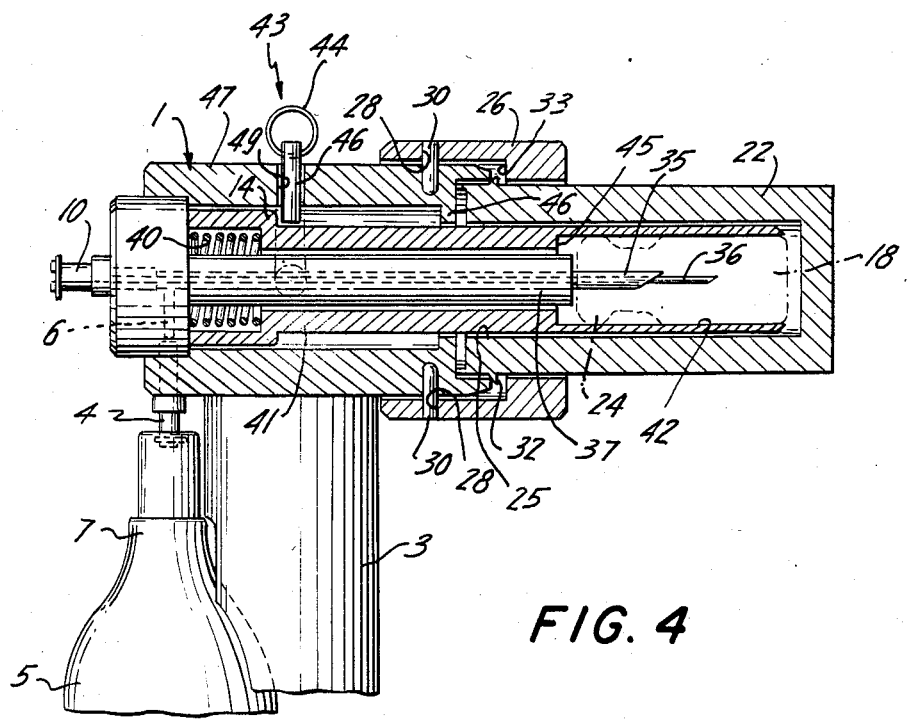
FIG. 4 is a cross-sectional view along the line 2—2 of FIG. 1 with the vial placed upon the needles of the dispenser.

In FIG. 4, the casing 22 is inserted into the dispenser 1 and maintained in position by means of a ring 26. The casing and the ring are so configured and dimensioned that the casing 22 fits into the hollow ring 26 until lip 32 engages the inner shoulder 33 of the ring. In this manner, ring 26 engages the casing 22. The ring 26 contains two slots 28 on either side. When the casing 22 is inserted into the dispenser 1, slots 28 are for the purpose of engaging the studs 30 which protrude from the surface of the dispenser so as to releasably secure the casing 22 containing the vial 18 to the dispenser 1. In accordance with one embodiment of this invention, the casing 22 is first placed into the dispenser 1 and the ring 26 is slipped over the casing 22 to secure the casing 22 to the dispenser 1 by means of the studs 30. On the other hand, the casing 22 may be placed within the ring 26 so that its lip 32 is secured within the hollow of the hollow ring 26. The hollow ring 26 is then placed upon the dispenser 1 in a manner that the studs 30 of said dispenser are engaged with the recesses 28 to secure the ring and lead shield contained therein to the dispenser 1.

Figure 3:
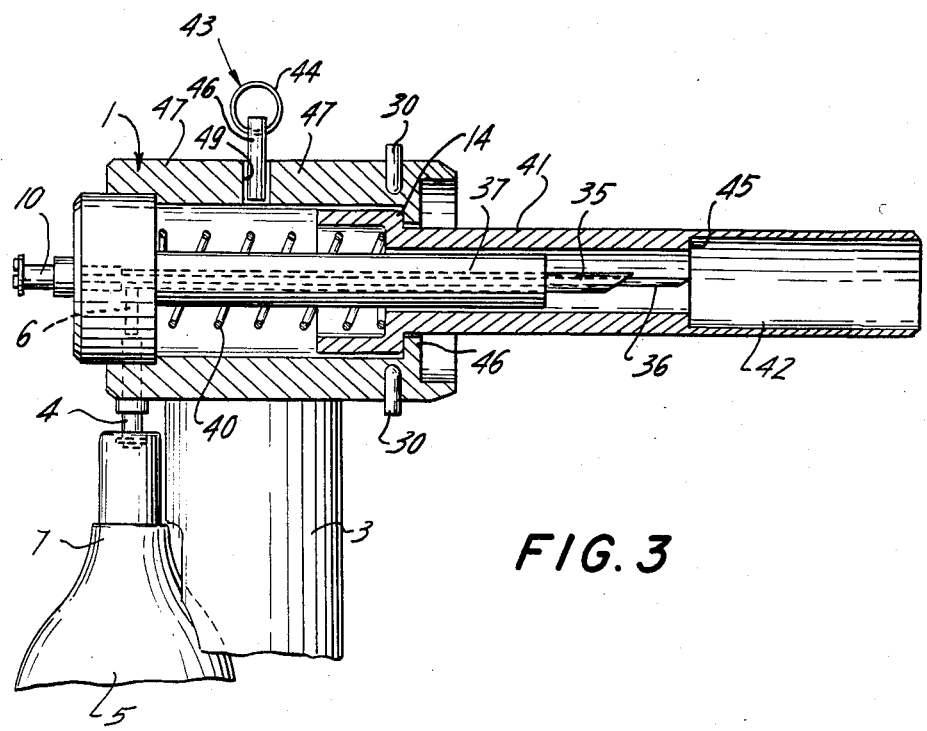
FIG. 3 is a cross-sectional view of the dispenser along line 2—2 of FIG. 1 after the vial has been ejected and removed.

FIG. 3 illustrates the dispenser after the vial 18 has been removed from the dispenser. The dispenser 1 contains two concentric needles 35 and 36 which are mounted within the dispenser in member 37. While the needles 35 and 36 are shown as concentric, they may be mounted in a parallel relation to each other or by other convenient means. Needle 35 is connected to air intake adapter 4. Needle 36 is connected to the outlet adapter 10. When a displacement gas such as air is squeezed from the bulb 5, it passes through air intake adapter to the needle 35 to the vial 18. The xenon gas in vial 18 when pierced by needles 35 and 36 will pass through needle 36 and out through outlet 10 and into the breathing adapter 12. The needles 35 and 36 are adapted to puncture the septum 24 of the vial 18 when the casing 22 is fitted into the dispenser 1. The dispenser 1 contains a spring means 40. Within the dispenser is an elongated member 41 which protrudes from the dispenser 1. This elongated member contains a flange 14 at one end through which a portion of the spring 40 is fitted. The elongated member is open at the other end 42 to surround needles 35 and 36 within this opening. When spring 40 is contracted as in FIG. 4, the needles 35 and 36, are in position to puncture the septum 24 of the vial enclosed in lead shield 22 so as to communicate with the interior of the vial with the air intake adapter 4 through needle 35 and the outlet 10 with needle 36.

The elongated member 41 is moveable within dispenser 1 by means of the action of the spring 40. When elongated member 41 is contracted against the springs in FIG. 4, the needles 35 and 36 are exposed to the interior of the vial. The moveable elongated member 41 is kept in this position by means of a locking mechanism 43 in the outer wall 47 of the dispenser 1. The outer wall 47 of the dispenser contains a flange 46 for engaging the flange 14 of the elongated member 41 when the spring 40 is extended. The elongated member 41 contains a lip 45 which engages the vial 18 when it enters the elongated member 41. The elongated member 41 is configured and dimensioned so that it enters the opening of the lead shield 22 and allows the vial to enter the opening 42 to engage the lip 45. In this position, the lead shield 22 surrounds the elongated member 41 as in FIG. 4.

In operating the dispenser of this invention, the elongated member 41 is locked into the position shown in FIG. 4 by means of the locking mechanism 43 which includes a split ring 44 and pin 46, which pin passes through a channel 49 in outer wall 47 and into contact with flange 14 of elongated member 41 to keep the elongated member compressed against spring 40. The casing 22 containing the vial 24 is then placed on dispenser 1 so that the vial 18 impinges against the needles 35 and 36 which are exposed due to the engagement of the locking means 43 with the flange 14 to prevent the spring 40 from moving member 41 to cover the needles 35 and 36. By placement of the casing 22 over the elongated member 41, the member 41 moves inside the casing so that the vial is engaged within the opening 42 of member 41. This opening 42 acts as a guide for the vial to position it against the needle elements 35 and 36. When the casing 22 is moved by hand on the elongated member 41, the fitting of the casing 22 over the elongated member 41 causes the needles 35 and 36 to rupture the septum and penetrate into the interior of the vial 18. The vial comes to rest within hollow 42 against the lip 45 of the elongated member 41. The lip 45 prevents the vial from moving further through the hollow 42 of elongated member 41.

The displacing gas such as air is pumped into the vial 18 from bulb 5 through needle 35. This displacement gas forces the xenon gas out of the vial through needle 36 into outlet 10.

In accordance with the preferred embodiment of this invention, the casing 22 is maintained in position on the dispenser 1 by means of ring 26. Ring 26 can be placed on the casing 22 prior to casing 22's placement on the dispenser 1. On the other hand, ring 26 can be used to guide the shield 22 onto the dispenser. Ring 26 maintains the shield in the position shown in FIG. 4 by fitting the stud 30 of the dispenser 1 in the recess 28 of the ring 26. This locks the lead shield in the position where the needles 35 and 36 penetrate the septum 24 of the vial 18 to extend within the interior of the vial.

After all of predetermined dose of the radioactive gas has been dispensed from the vial through the outlet 10, the needles 35 and 36 can be automatically ejected from the vial by releasing the locking means 43 and disengaging the studs 30 from the recesses 28 of the ring 26. In this manner, the spring 40 will cause the elongated member 41 to move outwardly. Flange 45 carried by the elongated member 41 which abuts the vial 18 will cause the vial 18 to move outwardly away from the needles. In this manner, needles 35 and 36 will disengage from the septum so that the casing and vial contained therein can be easily removed from the dispenser. Furthermore in this manner, there is no need to manually disengage the needles 35 and 36 from the septum of the vial.

It is apparent that many modifications can be made in accordance with this invention. If desired, a device can be constructed wherein the locking means 43 is removed. In such a device, the ring 26 through releasable engagement with the dispenser 1 can be used for retaining the vial against the action of the spring in the position shown in FIG. 4.

We claim:

1. A device for dispensing a radioactive gas contained in a sealed vial having a pierceable septum wherein the sealed vial is enclosed in a protective casing having an opening surrounding said septum, said device comprising
   (a) a dispenser having a outlet for dispensing said radioactive gas from said device and an inlet for feeding a displacement gas into said device;
   (b) first needle means protruding from said dispenser operably connected to said inlet, a second needle means protruding from said dispenser and operably connected to said outlet, both said needle means having end portions which protrude from said dispenser for piercing the septum of said vial and extending into the vial;
   (c) displacement gas injection means, including a source for said displacement gas connected to said inlet;
   (d) a spring means located in said dispenser;
   (e) an elongated member protruding from said dispenser, said elongated member having an opening at one end and being movably activated in said dispenser by said spring means, said elongated member being positioned in said dispenser to surround said protruding ends of both of said needle means, said elongated member configurated to fit into said opening of the protective casing to engage the vial within said opening of the elongated member;
   (f) means within the opening of said elongated member to engage the vial against the action of the spring means when both of the protruding ends of the needle means are positioned to pierce the septum and extend into the vial;
   (g) releasable locking means for maintaining the vial within the dispenser positioned against the action of the spring means so that both said needle means pierce the septum and extend into the vial, said locking means being adapted upon release to allow the vial to disengage from the needles through the action of the spring means.

2. The device of claim 1 wherein the protruding ends of said needle means are concentric.

3. The device of claim 1 wherein said locking means is adapted to fit around said protective casing.

4. The device of claim 3 wherein the said locking means contains a means adapted to releasably engage the surface of said dispenser.

5. The device of claim 4 wherein the locking means contains an opening for engaging the surface of the dispenser through a protuberance on said surface.

6. The device of claim 1 wherein said device contains a one-way valve means connected to said inlet for preventing substantive flow of a premeasured amount of radioactive gas from said valve to said source of displacement gas, but permitting flow of said displacement gas to said vial from said displacement gas source.

7. The device of claim 1 wherein said dispenser further includes a rigid means and said source is a flexible bulb positioned adjacent said rigid means, to allow the bulb to be collapsed against the surface of said rigid means.

8. The device of claim 7 wherein the rigid means extends from said dispenser and is shaped to provide a hand gripping configuration whereby the flexible bulb can be collapsed by squeezing said flexible bulb against said rigid means.

9. The device of claim 8 wherein said needle means are concentric.

10. The device of claim 9 wherein said locking means is adapted to fit around said protective casing.

11. The device of claim 10 wherein the said locking means contains a means adapted to releasably engage the surface of said dispenser.

12. The device of claim 11 wherein the locking means contains an opening for engaging the surface of the dispenser through a protuberance on said surface.

* * * * *